United States Patent
Gu

(10) Patent No.: US 9,034,909 B2
(45) Date of Patent: May 19, 2015

(54) USE OF ORGANIC COMPOUND FOR THE TREATMENT OF NOONAN SYNDROME

(75) Inventor: Jessie Gu, Fiorham Park, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/239,165

(22) PCT Filed: Aug. 29, 2012

(86) PCT No.: PCT/US2012/052750
§ 371 (c)(1),
(2), (4) Date: Feb. 17, 2014

(87) PCT Pub. No.: WO2013/033133
PCT Pub. Date: Mar. 7, 2013

(65) Prior Publication Data
US 2014/0200249 A1    Jul. 17, 2014

Related U.S. Application Data

(60) Provisional application No. 61/530,128, filed on Sep. 1, 2011.

(51) Int. Cl.
*A61K 31/4184*    (2006.01)
*C07D 235/08*    (2006.01)
*A61K 31/416*    (2006.01)

(52) U.S. Cl.
CPC ............ *C07D 235/08* (2013.01); *A61K 31/416* (2013.01)

(58) Field of Classification Search
USPC ........................................ 514/394; 548/304.4
See application file for complete search history.

(56) References Cited

FOREIGN PATENT DOCUMENTS

| WO | 03/077914 | 9/2003 |
|---|---|---|
| WO | 2008/022335 | 2/2008 |
| WO | 2009/135000 | 11/2009 |

OTHER PUBLICATIONS

Dahlgren, J., GH Therapy in Noonan Syndrome: Review of Final Height Data, vol. 72, No. Suppl. 2, pp. 46-48, 2009.

*Primary Examiner* — Kristin Vajda
(74) *Attorney, Agent, or Firm* — Gregory Ferraro

(57) ABSTRACT

The use of a MEK inhibitor compound of Formula (I), as defined herein, or a pharmaceutically acceptable salt thereof for the preparation of a medicament for the treatment of Noonan Syndrome, a method of treating a warm-blooded animal, especially a human, having Noonan Syndrome, comprising administering to said animal a therapeutically effective amount of a MEK inhibitor compound of Formula (I), as defined herein, or a pharmaceutically acceptable salt thereof; and to a pharmaceutical composition and a commercial package comprising a compound of Formula (I) or a pharmaceutically acceptable salt thereof, and a package insert or other labeling including directions for treating Noonan Syndrome.

6 Claims, No Drawings

USE OF ORGANIC COMPOUND FOR THE TREATMENT OF NOONAN SYNDROME

The present invention relates to the use of a MEK inhibitor compound of Formula (I), as defined herein, or a pharmaceutically acceptable salt thereof for the preparation of a medicament for the treatment of Noonan Syndrome, a method of treating a warm-blooded animal, especially a human, having Noonan Syndrome, comprising administering to said animal a therapeutically effective amount of a MEK inhibitor compound of Formula (I), as defined herein, or a pharmaceutically acceptable salt thereof; and to a pharmaceutical composition and a commercial package comprising a compound of Formula (I) or a pharmaceutically acceptable salt thereof, and a package insert or other labeling including directions for treating Noonan Syndrome.

The term "Noonan Syndrome", also known as Turner-like Syndrome, as used herein is a type of genetic disorder that prevents normal development in multiple parts of the body and first described by J. A. Noonan and D. A. Ehmke in 1963. Noonan Syndrome is characterized by short stature, congenital heart defect (pulmonic stenosis), hypertrophic cardiomyopathy, developmental delays, chest deformities, impaired blood clotting, and/or a characteristic configuration of facial features, including but not limited to broad or webbed neck, wide-set eyes and/or low ears. (See, e.g., Allanson, Journal of Medical Genetics, 1987, 24:9-13; Noonan J. A. and Ehmke D. A. J. Pediatr., 1963, 63:468-70.)

Noonan syndrome is the most common cause of neonatal hypertrophic cardiomyopathy, with a prevalence of 1 in 1000-2500 live births. Genetic defects in the Ras-Raf-Mek-Erk pathway (MEK, KRAS, PTPN11, RAF1, SOS1 genes) have been identified to cause Noonan syndrome. About 20% of the Noonan syndrome patients have hypertrophic cardiomyopathy. In one natural history study of the disease, about 40% Noonan syndrome HCM patients died or required cardiac surgery during a 12 year follow up (Shaw et al. Arch. Dis. Child, 2007, 92:128-132). In Noonan syndrome patients with hypertrophic cardiomyopathy, activation of MEK and ERK occurs downstream from mutations in the genes upstream to or in MEK. Randomized controlled trials with anti-hypertensives have shown that reversal of left ventricular hypertrophy (LVH) is associated with better cardiovascular morbidity and mortality outcome. However, there remains a major unmet medical need in Noonan Syndrome patients with limited medical treatment options mainly to relieve symptoms, and there is still a large unmet medical need to improve patient survival.

The compound of Formula (I), as defined herein, is a potent and highly selective inhibitor of mitogen-activated protein kinase/extracellular signal-regulated kinase kinase (MEK). MEK is a major protein in the RAS/RAF/MEK/ERK pathway, which signals toward cell proliferation and survival. The compound of Formula (I) has potent inhibitory activity against the MEK1 and MEK2 proteins and targets the RAS/RAF/MEK/ERK pathway which is involved in cardiomyocyte growth regulation.

It has been found that the compound of Formula (I), as defined herein, is useful in the treatment of Noonan Syndrome.

Hence, the invention relates to the use of the compound of Formula (I) or a pharmaceutically acceptable salt thereof for the preparation of a medicament for the treatment of Noonan Syndrome.

In one aspect, the invention relates to a compound of Formula (I) or a pharmaceutically acceptable salt thereof for use in the treatment of Noonan Syndrome.

In one embodiment of this aspect Noonan Syndrome is a genetic development disorder characterized by short stature, congenital heart defect (pulmonic stenosis), hypertrophic cardiomyopathy, developmental delays, chest deformities, impaired blood clotting, and a characteristic configuration of facial features, including but not limited to broad or webbed neck, wide-set eyes and/or low ears.

In another embodiment of this aspect said compound of Formula (I) is for use in the treatment of a warm-blooded animal in need thereof suffering from Noonan Syndrome.

In one embodiment said warm-blooded animal is a human.

The MEK inhibitor compound of particular interest for use in the present invention is an alkylated benzimidazole derivative compound described by the Formula (I):

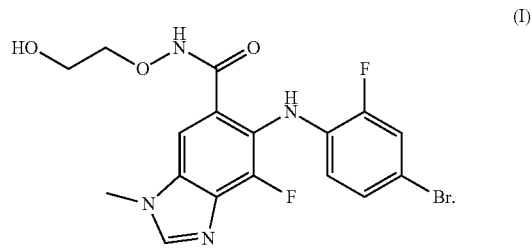 [SMILES: Cn1cnc2c(F)c(Nc3ccc(Br)cc3F)c(C(=O)NOCCO)cc21]

The compound of Formula (I) is 6-(4-bromo-2-fluorophenylamino)-7-fluoro-3-methyl-3H-benzoimidazole-5-carboxylic acid (2-hydroxyethoxy)-amide (COMPOUND A). The compound of Formula (I) is described in PCT Application No. WO 03/077914, which is hereby incorporated by reference in its entirety hereto, and methods for its preparation have been described, for example, in Example 18 therein. The compound of Formula (I) has been shown to be a potent MEK inhibitor. (See PCT Application No. WO 03/077914 at page 37.) Further, in an isolated enzyme assay, the compound 6-(4-bromo-2-fluorophenylamino)-7-fluoro-3-methyl-3H-benzoimidazole-5-carboxylic acid (2-hydroxyethoxy)-amide (COMPOUND A) inhibited MEK1 with a 50% inhibition ($IC_{50}$) value of 12 nanomolar (nM).

The compounds used in the present invention may possess one or more asymmetric centers and can be produced as individual (R)- or (S)-stereoisomers or as mixtures thereof as described in PCT Application No. WO 03/077914. Except as otherwise indicated, the description or naming of a particular compound in the specification and claims is intended to include both individual enantiomers, diastereomeric mixtures, racemic or otherwise, thereof. Accordingly, this invention also includes all such isomers, including diasteroemeric mixtures and resolved enantiomers of the compounds of this invention. Diastereomieric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g. hydrolyzing) the individual diastereomers to the corresponding pure enantiomers. The methods for the determination of stereochemistry and the separation of stereoisomers are well known in the art (see discussion in Chapter 4 of "Advanced organic Chemistry", 4$^{th}$ edition, J. March. John Wiley and Sons, New York, 1992).

The compounds of the invention may be administered in free form or in pharmaceutically acceptable salt form.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

A "salt", as used herein, unless otherwise indicated, includes salts of acidic and basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzoate, bromide, chloride, citrate, fumarate, hydrobromide, hydrochloride, iodide, lactate, maleate, mandelate, nitrate, oxalate, salicylate, succinate, and tartrate salts. Since a single compound of the present invention may include more than one acidic or basic moieties, the compounds of the present invention may include mono, di or tri-salts in a single compound.

In the case of an acidic moiety in a compound of the present invention, a salt may be formed by treatment of a compound of the present invention with a basic compound, particularly an inorganic base. Preferred inorganic salts are those formed with alkali alkaline earth metals such as lithium, sodium, potassium, barium, and calcium. Preferred organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine. An especially preferred salt is a sodium or potassium salt of a compound of the present invention.

With respect to basic moieties, a salt is formed by the treatment of a compound of the present invention with an acidic compound, particularly an inorganic acid. Preferred inorganic salts of this type may include, for example, the hydrochloric, hydrobromic, sulfuric, phosphoric or the like salts. Preferred organic salts of this type, may include, for example, salts formed with acetic succinic, citric, maleic, fumaric, D-glutamic, glycolic, benzoic, cinnamic and the like organic acids. An especially preferred salt of this type is a hydrochloride or sulfate salt of COMPOUND A of the present invention.

Additional pharmaceutically acceptable salts of COMPOUND A suitable for the present invention include the salts disclosed in PCT Application No. WO 03/077914, which is hereby incorporated into the present application by reference.

Furthermore, the invention relates to a method of treating Noonan Syndrome, comprising administering a therapeutically effective amount of a compound of Formula (I) or a pharmaceutically acceptable salt thereof to a warm-blooded animal, in particular a human, in need thereof.

The term "treating" or "treatment" as used herein comprises a treatment relieving, reducing or alleviating at least one symptom in a subject or effecting a delay of progression of Noonan Syndrome. For example, treatment can be the diminishment of one or several symptoms of Noonan Syndrome or complete eradication of Noonan Syndrome. Within the meaning of the present invention, the term "treat" also denotes to arrest, delay the onset (i.e., the period prior to clinical manifestation of a disease) and/or reduce the risk of developing or worsening of Noonan Syndrome.

The term "therapeutically effective amount" or "clinically effective amount" as used herein is an amount sufficient to provide an observable improvement over the baseline clinically observable signs and symptoms of Noonan Syndrome in a warm-blooded animal, preferably human, treated with the therapeutic agent.

The term "warm-blooded animal" as used herein includes animals, which are capable of suffering from or afflicted with Noonan Syndrome. Examples of warm-blooded animals include mammals, e.g., humans, dogs, cows, horses, pigs, sheep, goats, eats, mice, rabbits rats, etc. In the preferred embodiment, the subject is a human, e.g., a human suffering from, at risk of suffering from, or potentially capable of suffering from Noonan Syndrome.

The present invention provides a method of treating Noonan Syndrome comprising administering a compound of Formula (I) for a pharmaceutically acceptable salt thereof in an amount which is therapeutically effective against Noonan Syndrome to a warm-blooded animal in need thereof.

The person skilled in the pertinent art is fully enabled to select relevant test models to prove the hereinbefore and hereinafter mentioned beneficial effects on Noonan Syndrome a compound of Formula (I) or a pharmaceutically acceptable salt thereof inhibiting the MEK activity. The pharmacological activity of a compound of Formula (I) or a pharmaceutically acceptable salt thereof may e.g., be demonstrated in a suitable clinical study or by means of the Examples described below.

Suitable clinical studies are in particular, for example, open label, dose escalation studies in patients suffering from Noonan Syndrome. The beneficial effects on Noonan Syndrome may be determined directly through the results of these studies which are known as such to a person skilled in the art. Such studies may be, in particular, be suitable to compare the effects of the MEK inhibitor compound of Formula (I) or pharmaceutically acceptable salt thereof in monotherapy against prior available treatments, e.g., growth hormone to treat the short stature in some patients with Noonan Syndrome. Each patient may receive doses of a MEK inhibitor compound of Formula (I) or pharmaceutically acceptable salt thereof either daily or intermittently and/or either in a single or multiple unit dosage forms. The efficacy of the treatment may be determined in such studies, e.g., after 12, 18 or 24 weeks by evaluation of symptom scores every 6 weeks.

Furthermore, the invention relates to a pharmaceutical composition comprising the compound of Formula (I) or a pharmaceutically acceptable salt thereof for use in the treatment of warm-blooded animal in need thereof suffering from Noonan Syndrome. The term "pharmaceutical composition" is defined herein to refer to a mixture or solution containing at least one therapeutic agent to be administered to a warm-blooded animal, preferably a human, in order to treat the Noonan Syndrome affecting the mammal.

The pharmaceutical compositions may be prepared in a manner known per se and are those suitable for enteral, such as oral or rectal, and parenteral administration to warm-blooded animals, including humans, comprising a therapeutically effective amount of the compound of Formula (I) or a pharmaceutically acceptable salt thereof alone or in combination with one or more pharmaceutically acceptable carriers, especially suitable for enteral or parenteral application.

The novel pharmaceutical composition may contain, from about 0.1% to about 99.9%, preferably from about 1% to about 60%, of the therapeutic agent(s). The term "about" or "approximately", as used herein in each instance, shall have the meaning of within 10%, more preferably within 5%, of a given value or range.

Suitable pharmaceutical compositions for enteral or parenteral administration are, for example those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, or fabrication techniques readily apparent to those skilled in the art. A unit dosage form containing the compound of Formula (I) or a pharmaceutically acceptable salt thereof may be in the form of micro-tablets enclosed inside a capsule, e.g. a gelatin capsule. For this, a gelatin capsule as is employed in pharmaceutical formulations can be used, such as the hard gelatin capsule known as CAPSUGEL, available from Pfizer.

The unit dosage forms of the present invention may optionally further comprise additional conventional carriers or excipients used for pharmaceuticals. Examples of such carriers include, but are not limited to, disintegrates, binder, lubricants, glidants, stabilizers, and fillers, diluents, colorants, flavours and preservatives. One of ordinary skill in the art may select one or more of the aforementioned carriers with respect to the particular desired properties of the dosage form by routine experimentation and without any undue burden. The amount of each carrier used may vary within ranges conventional in the art. The following references which are all hereby incorporated by reference disclose techniques and excipients used to formulate oral dosage forms. See *The Handbook of Pharmaceutical Excipients*, 4$^{th}$ edition. Rowe et a., Eds., American Pharmaceuticals Association (2003); and *Remington: the Science and Practice of Pharmacy*, 20$^{th}$ edition, Gennaro, Ed., Lippincott Williams & Wilkins (2003).

These optional additional conventional carriers may be incorporated into the oral dosage form either by incorporating the one or more conventional carriers into the initial mixture before or during granulation or by combining the one or more conventional carriers with granules comprising the combination of agents or individual agents of the combination of agents in the oral dosage form. In the latter embodiment, the combined mixture may be further blended, e.g., through a V-blender, and subsequently compressed or molded into a tablet, for example a monolithic tablet, encapsulated by a capsule, or filled into a sachet.

Examples of pharmaceuticals acceptable disintegrates include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.): cross-linked sodium carboxymethylcellulose or croscarmellose sodium, e.g., AC-DI-SOL from FMC; and cross-linked calcium carboxymethylcellulose; soy polysaccharides; and guar gum. The disintegrate may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol powdered cellulose and microcrystalline cellulose. The lubricant may be present in an amount from about 0% to about 10% weight of the composition. In one embodiment, the lubricant may be present in an amount from about 0.1% to about 1.5% weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactase, mannitol, microcrystalline cellulose, pondered cellulose, sorbitol sucrose and talc. The filler and/or diluent, e.g., may be present in an amount from about 0% to about 80% by weight of the composition.

The effective dosage of the compound of Formula (I) or a pharmaceutically acceptable salt thereof may vary depending on the particular compound or pharmaceutical composition employed, the mode of administration, the condition being treated, and the severity of the condition being treated. Thus, the dosage regimen of the compound of Formula (I) or a pharmaceutically acceptable salt thereof is selected in accordance with a variety of factors including the route of administration and the renal and hepatic function of the patient. A clinician or physician of ordinary skill can readily determine and prescribe the effective amount of the therapeutic agent required to alleviate, counter or arrest the progress of the condition. The optimum dosage or concentrations of the compound of Formula (I) or a pharmaceutically acceptable salt thereof that yield efficacy without toxicity are based on the kinetics of the therapeutic agent's availability to target sites, and are determined using methods known to those of skill in the art.

The MEK inhibitor compound of Formula (I) or a pharmaceutically acceptable salt thereof may be administered to a suitable subject daily in single or divided doses at an effective dosage in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day.

The optimal dosage of the compound of Formula (I) or a pharmaceutically acceptable salt thereof for treatment of Noonan Syndrome can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of the compound of Formula (I) or a pharmaceutically acceptable salt thereof that may be combined with the carrier materials to produce a single dosage form will vary depending upon the individual treated and the particular mode of administration.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Furthermore, the invention relates to a commercial package comprising a compound of Formula (I) or a pharmaceutically acceptable salt thereof, and a package insert or other labeling including directions for treating Noonan Syndrome by administering a compound of Formula (I) or a pharmaceutically acceptable salt thereof to a patient in need thereof. In the preferred embodiment, the package insert or other labeling including directions for treating Noonan Syndrome by administering a therapeutically effective amount of the compound of Formula (I) or a pharmaceutically acceptable salt thereof to a patient in need thereof.

The effectiveness of the compound of Formula (I) or a pharmaceutically acceptable salt thereof of the present invention can be shown by a number of well-established tests/models, including but not limited to an open-label clinical study in patients suffering with Noonan Syndrome. A non-limiting example of a suitable open-label clinical study in patients suffering with Noonan Syndrome is provided hereto:

EXAMPLE 1

Approximately eighteen (18) to thirty (30) male and female patients diagnosed with Noonan Syndrome are enrolled to participate in the clinical study and randomized. At least twelve (12) patients are expected to complete the study.

Patients that are enrolled in the study include male and female patients suffering from Noonan Syndrome with confirmed cardiac hypertrophy, age 18 to 65 years of age, and in general good health as determined by past medical history, physical examination, vital signs, electrocardiogram, and laboratory tests at screening. Cardiac hypertrophy is defined by left ventricular wall thickness greater than or equal to 12 mm by echocardiography or MRI, or the change in wall thickness is accompanied by an associated increase in left ventricular mass which is defined by echo or MRI as greater than 134 $g/m^2$ and 110 $g/m^2$ in men and women, respectively. The enrolled patients have a weight of at least 45 kg and a body mass index (BMI) within the range of 18-34 $kg/m^2$. Excluded from the study are patients having any of the following: (a) primary Long QT syndrome or a history of significant ECG abnormalities, (b) history of malignancy of any organ system (other than localized basal cell carcinoma of the skin) within the past 5 years, (c) women of child-bearing potential unless using highly effective contraception during the study and for 5 half lives after stopping treatment, (d) sexually active males unless using effective protection during intercourse during the study period, for 5 half lives after stopping treatment and not fathering a child in this period, or (e) use of any prescription drugs other than beta-blockers, diuretics, CCB, amiodarone, disopyramide, herbal supplements, within four (4) weeks prior to initial dosing, and/or over-the-counter (OTC) medication, dietary supplements (vitamins included) within two (2) weeks prior to initial dosing. If needed (i.e, an incidental and limited need), paracetamol or acetaminophen is acceptable, but must be documented.

The study will include a 21-day screening period, one baseline period, and one treatment period of six (6) months. Subjects who meet the eligibility criteria at screening are admitted to baseline evaluations. All baseline safety evaluation results are available prior to dosing. Subjects are admitted to the study site approximately 12 hours prior to dosing for baseline evaluations. Following the first dose of the Study Medication, pharmacokinetic, pharmacodynamic, and safety assessments are made for up to 12 hours prior to the next dose of Study Medication. Dosing b.i.d. will continue for 6 months with assessments performed as per the assessment schedule. The dose for all patients is 45 mg b.i.d. but can be adjusted to 60 mg b.i.d. or 30 mg b.i.d. based on safety and tolerability observed. Upon completion of the 6 months treatment, patients undergo study completion evaluations and then are discharged from the study. Patients are domiciled for 24 hours post-dose on day 1 and day 8. For the remainder of the study, patients return to the site for assessments.

Safety assessments include physical examinations, ECGs, vital signs, standard clinical laboratory evaluations (hematology, blood chemistry, urinalysis), ophthalmological exams, adverse event and serious adverse event monitoring. At screening and baseline, the patient satisfy the following criteria in the sitting position after resting for three (3) minutes: oral body temperature between 35.0-37.5° C., systolic blood pressure, 90-140 mm Hg, diastolic blood pressure, 50-90 mm Hg, and pulse rate, 40-90 bpm. During the screening and baseline, the patient satisfy the following criteria after three (3) minutes in the standing position: (a) no more than a 20 mm Hg drop in systolic or 10 mm Hg drop in diastolic blood pressure, and (b) increase in heart rate greater than 20 bpm, and with no manifestations of postural hypotension.

Efficacy assessments include cardiac structural and functional measurements by magnetic resonance imaging (MRI) and cardiac energetic assessment by P-31 magnetic resonance spectroscopy (MRS).

For the treatment period of the study, the compound of Formula (I) or a pharmaceutically acceptable salt thereof (referred to as "Study Medication") will be administered to the enrolled patients in the dose of 45 mg b.i.d. The Study Medication is prepared in 15 mg tablets and supplied to the Investigator as individual subject packs. The Study Medication is administered to the patient as follows:
  (a) During the patient's visit to the Study Center, study center personnel administer the Study Medication with 240 mL of water in the morning between 07:00 and 09:30 following an overnight fast. Each patient's mouth is checked to ensure that the medication was swallowed.
  (b) During periods where the patient is not on-site, the investigator promote compliance by instructing the patient to take the study drug exactly as prescribed and by stating that compliance is necessary for the patient's safety and the validity of the study. The patient is instructed to contact the investigator if he/she is unable for any reason to take the study drug as prescribed.
  (c) Patterns are instructed not to chew the medication, but to swallow it whole. For pharmacokinetic assessment days, subjects rest quietly in the upright position for the next 4 hours after the morning dose unless performing a study assessment, e.g. ECG.

The patient are evaluated at the Study Center on Days 1, 2, 8, 9, 15, 28, 56, 84, 140, 182 and 185 of the treatment period. All dosages prescribed and dispensed to the subject and all dose changes during the study are recorded on the Dosage Administration Record CRF (CRF)/

Treatment are put on hold or stopped if any of the following criteria are met: (a) 1 Study Medication-related Serious Adverse Event is reported, (b) at least 4 subjects in the treatment group experience a similar unanticipated Adverse Event which is assessed as either moderate or severe in intensity, and is potentially related to Study Medication, or (c) if 4 retinal events or 4 stomatitis/mucositis of grade 3/4, or 2 CK elevation >2000 U/L are experienced in the enrolled patients.

Prior to and while the patient receives treatment with the Study Medication, the following characteristics are assessed for each patient: demographics, relevant medical history/current medical condition. Hepatitis B and C screen, HIV screen, alcohol test, drug screen, urine cotinine level determination, cardiac magnetic resonance (CMR) imaging to assess structural changes in the myocardial mass and thickness, resting myocardial ratio of phosphocreatine to adenosine triphosphate (PCr/ATP) will be assessed with cardiac 31P nuclear magnetic resonance spectroscopy, pERF/ERK assessment in whole blood samples by flow cytometry, a full physical examination, electrocardiogram (ECG), pregnancy, opthalmic examination, and pharmacokinetic analysis of venous blood samples. Pharmacokinetic parameters include Ctrough, Cmax, Tmax, AUC0-12 h, AUClast, Racc (i.e, the accumulation ratio calculated using AUC values obtained from a dosing interval or determined based on a ratio of single dose and steady state predose concentration values), the degree of fluctuation calculated as Cmax,ss−Cmin,ss)/Cav,ss at steady state (Fluc), and any metabolite to parent ratio on Day 1 and Day 8. PCr/ATP comparisons are performed between and 3 months or 6 months to detect any significant changes.

All patients receiving at least one dose of the Study Medication are evaluated to assess the overall safety and PK/PD parameters. The following variables are evaluated to demonstrate the efficacy of the Study Medication for the treatment of the Noonan Syndrome patients: (a) hypertrophy regression after 6 months treatment by measuring left ventricular mass (LVM) and left ventricular mass index (LVMi) at baseline, 3 and 6-months by MRI, (b) cardiac energetic state represented by PCr/ATP ratio at baseline, 3 and 6 months treatment by use of phosphorus-31 magnetic resonance spectroscopy. Since left ventricular mass and thickness are derived from an overall cardiac MR evaluation, the following additional hemodynamic and functional parameters are secondary endpoints: end-systolic and end-diastolic right and left ventricular volumes, stroke volume, ejection traction, cardiac output and cardiac index. These parameters are derived from cine breath-hold MR images acquired over the cardiac cycle. Further, with the use of Gd-DTPA contrast agent in the cardiac MR protocol, myocardial perfusion and degree of fibrosis can be assessed.

With the foregoing clinical trial study, it is demonstrated that the compounds of Formula (I) or a pharmaceutically acceptable salt thereof are useful in the treatment of patients suffering from Noonan Syndrome.

The invention claimed is:

1. A method of treating Noonan Syndrome comprising administering a therapeutically effective amount of a compound of Formula (I)

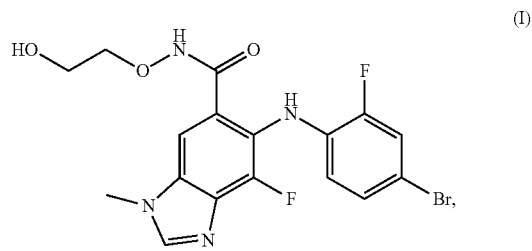 [SMILES: Cn1cnc2c(F)c(Nc3ccc(Br)cc3F)c(C(=O)NOCCO)cc21]

or a pharmaceutically acceptable salt thereof to a warm-blooded animal in need thereof.

2. A method of treating Noonan Syndrome according to claim 1, wherein the Noonan Syndrome is a genetic development disorder characterized by short stature, congenital heart defect (pulmonic stenosis), hypertrophic cardiomyopathy, developmental delays, chest deformities, impaired blood clotting, and a characteristic configuration of facial features, including but not limited to broad or webbed neck, wide-set eyes and/or low ears.

3. A method of treating Noonan Syndrome according to claim 1, wherein the warm-blooded animal is a human.

4. A commercial package comprising (i) a compound of Formula (I)

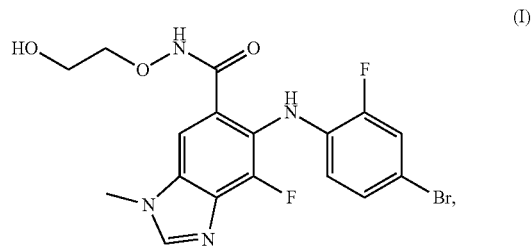 [SMILES: Cn1cnc2c(F)c(Nc3ccc(Br)cc3F)c(C(=O)NOCCO)cc21]

or a pharmaceutically acceptable salt thereof for use in the treatment of warm-blooded animal suffering from Noonan Syndrome, and (ii) a package insert or other labeling including directions for treating Noonan Syndrome by administering a compound of Formula (I) or a pharmaceutically acceptable salt thereof to a patient in need thereof.

5. A commercial package according to claim 4, wherein the Noonan Syndrome is a genetic development disorder characterized by short stature, congenital heart defect (pulmonic stenosis), hypertrophic cardiomyopathy, developmental delays, chest deformities, impaired blood clotting, and a characteristic configuration of facial features, including but not limited to broad or webbed neck, wide-set eyes and/or low ears.

6. A commercial package according to claim 4, wherein the warm-blooded animal is a human.

* * * * *